United States Patent
Jarvis

(10) Patent No.: US 9,592,193 B2
(45) Date of Patent: Mar. 14, 2017

(54) CANINE SEBUM SUBSTITUTE

(71) Applicant: David Paul Jarvis, Spencer, WV (US)

(72) Inventor: David Paul Jarvis, Spencer, WV (US)

(73) Assignee: Pet Research Labs, LLC, Ormond Beach (PL)

( * ) Notice: Subject to any disclaimer, the term of this patent is extended or adjusted under 35 U.S.C. 154(b) by 0 days.

(21) Appl. No.: 14/120,364

(22) Filed: May 15, 2014

(65) Prior Publication Data
US 2015/0328136 A1 Nov. 19, 2015

(51) Int. Cl.
| | |
|---|---|
| *A61K 8/92* | (2006.01) |
| *A61K 8/97* | (2006.01) |
| *A61Q 5/02* | (2006.01) |
| *A61Q 19/10* | (2006.01) |
| *A61Q 5/00* | (2006.01) |
| *A61K 8/63* | (2006.01) |
| *A61K 8/49* | (2006.01) |
| *A61Q 5/12* | (2006.01) |

(52) U.S. Cl.
CPC .............. *A61K 8/922* (2013.01); *A61K 8/498* (2013.01); *A61K 8/63* (2013.01); *A61K 8/92* (2013.01); *A61K 8/97* (2013.01); *A61Q 5/00* (2013.01); *A61Q 5/02* (2013.01); *A61Q 5/12* (2013.01); *A61K 2800/5922* (2013.01)

(58) Field of Classification Search
CPC . A61K 8/92; A61K 8/922; A61K 8/63; A61K 8/498; A61K 2800/5922; A61K 8/97; A61Q 5/00; A61Q 5/02; A61Q 5/12; A61Q 19/10
See application file for complete search history.

(56) References Cited

U.S. PATENT DOCUMENTS

| | | | |
|---|---|---|---|
| 8,460,713 B2* | 6/2013 | Gammelsaeter | A61K 8/97 424/582 |
| 8,828,455 B2* | 9/2014 | Florence | A61K 8/97 424/725 |
| 9,474,709 B2* | 10/2016 | Sams | A61K 8/922 |
| 2013/0243706 A1* | 9/2013 | Barone | A61K 8/31 424/59 |
| 2014/0105844 A1* | 4/2014 | Brown | A61K 8/361 424/70.1 |

FOREIGN PATENT DOCUMENTS

AU 2011202873 A1 * 7/2011 ............... A23L 1/00

OTHER PUBLICATIONS

"Petology Sensitive Conditioner", King Wholesale Pet Supplies [online], no publication date given, [retrieved Sep. 29, 2015] Retrieved from the Internet: <URL: http://www.kingwholesale.com/Shopping/ProductInfo.cfm?Item=31186>.*
Tapio Nikkari, "Comparative Chemistry of Sebum," 1974; The Journal of Investigative Dermatology, 62:257-267.*

* cited by examiner

*Primary Examiner* — John Pak
(74) *Attorney, Agent, or Firm* — Arthur W. Fisher, III

(57) ABSTRACT

A canine sebum substitute utilizes plant derived raw components that contain essential fatty acids, triglycerides and sterols present in canine sebum applied directly to the coat or added to pet products such as shampoos, conditioners, shine sprays, and detanglers to re-fat the hair and skin of dogs and improve shine and condition.

10 Claims, No Drawings

CANINE SEBUM SUBSTITUTE

CROSS REFERENCE

This non-provisional application claims priority of provisional application Ser. No. 61/796,151 entitled Pet Hair Conditioning and Shine Composition filed on Nov. 5, 2012.

BACKGROUND OF THE INVENTION

The present invention is in the technical field of pet grooming and conditioning compositions. More particularly, the present invention is in the technical field of a naturally derived composition that emulates canine sebum with regard to composition and performance.

Canine sebum is produced in the sebaceous glands present in the skin of dogs. This oily mixture of fatty acids, sterols, triglycerides and other biological materials coats the hair and fur and performs a variety of functions at the skin and hair surfaces such as hair and skin conditioning, providing shine to the hair, providing elasticity to the hair and fur, waterproofing of the hair and skin and protection of hair and skin, as well as reduction of transepidermal water loss. Traditional grooming practices such as shampooing strip this natural sebum from the coats of pets such as dogs and leaves the hair/fur and skin vulnerable to the environment and lacking luster, shine and conditioning.

The present invention is a plant derived substitute for canine sebum that may be applied to the dog directly or added to pet grooming shampoos and conditioners, detanglers and maintenance products such as shine sprays that reproduces the performance and mimics the composition of canine sebum and re-fats the hair and skin. The present invention can be added to traditional products to replenish the natural oils that shampooing removes or it can be applied directly to the hair and fur of a dog (canine).

While some of the prior art may contain some similarities relating to the present invention, none of them teach, suggest or include all of the advantages and unique features of the invention disclosed hereunder.

SUMMARY OF THE INVENTION

The present invention is a naturally derived composition that utilizes raw materials to produce a composition that mimics canine sebum in performance and chemical composition and content.

The composition comprises about 42% plant sterol esters, about 25% jojoba oil, about 20% olive oil, about 7% safflower oil, about 5% almond oil, and about 1% tocopherol (plant derived).

Preferably, the composition comprises 42% plant sterol esters, 25% jojoba oil, 20% olive oil, 7% safflower oil, 5% almond oil, and 1% tocopherol (plant derived).

The invention accordingly comprises the features of construction, combination of elements, and arrangement of parts which will be exemplified in the construction hereinafter set forth, and the scope of the invention will be indicated in the claims.

BRIEF DESCRIPTION OF THE TABLES

For a fuller understanding of the nature and object of the invention, reference should be had to the following detailed description taken in connection with the tables in which:

Table 1 is a composition of the present invention.

Table 2 is an alternate embodiment of the composition of the present invention.

Table 3 is another alternate embodiment of the composition of the present invention.

Table 4 is the composition of the jojoba oil of the present invention.

Table 5 is the composition of the olive oil of the present invention.

Table 6 is the composition of the peanut oil of the present invention.

Table 7 is the composition of the safflower oil of the present invention.

DETAILED DESCRIPTION OF THE INVENTION

In mammals such as dogs (canines) the sebaceous glands are microscopic glands that secrete an oily/waxy substance that protects, waterproofs and softens (plasticizes) the skin and hair of mammals (keratin polymer). There is evidence to indicate that sebum offers antimicrobial activity to the skin surface and even certain essential vitamins such as vitamin E. Anti-inflammatory and pro-inflammatory activity can be demonstrated from sebum. Sebum and sebaceous secretions in conjunction with apocrine secretions also play a thermo-regulatory role in that in hot conditions emulsification of these combined secretions may prevent the loss of transepidermal water and prevent moisture loss. This can modify internal temperature. Sebum performs a very important evolutionary function on the hair and skin of dogs and is responsible for a healthy and attractive coat and skin.

The oily/waxy substance secreted by the sebaceous glands of dogs is called sebum. Sebum is derived from the Latin, meaning fat or tallow. The sebaceous glands are composed of very specialized cells that that produce sebum and as the cells fill with sebum, ultimately burst and release the sebum onto the skin and hair.

Sebum is composed of triglyceride oils, squalene, waxy diesters, fatty acids and other biological products of the fat producing cells in the sebaceous glands. The composition of canine sebum is unique and has a fatty acid/triglyceride/wax diester and other fat producing cell metabolite composition different from any other species of mammal. This unique composition of sebum is provides for its superior performance and protection of the hair and skin.

Modern shampoos remove naturally produced sebum from the hair and skin of dogs. This loss of sebum removes a critical natural component from the biological systems that protect the hair and skin, control internal temperature and protect the animal from the elements. It also makes the hair and skin drier and less pliable, reduces luster and conditioned feel. It is thereby important to reapply a sebum substitute that is as close to the composition of natural canine sebum as possible.

The present invention is a canine sebum substitute that contains many of the naturally occurring sterols, triglycerides, waxes, fats and oils present in canine sebum, thereby replacing the sebum necessary for proper biological function and beautification of hair and skin. The invention also contains plant derived ingredients. No substitute for canine sebum exists and no sebum substitute exists that is completely plant derived that can be used as is on the hair of canines or used as an additive for pet shampoos and conditioning and maintenance products.

Tables 1 through 7 identify the components of the present invention by percentages of weight.

It should also be noted the tocopherol acetate can be substituted for tocopherol.

TABLE 1

Canine Sebum Composition

| COMPONENTS | About % | Preferred % |
|---|---|---|
| Plant Sterol Esters | 42% | 42% |
| Jojoba Oil | 25% | 25% |
| Olive Oil | 20% | 20% |
| Peanut Oil | 7% | 7% |
| Almond Oil | 5% | 5% |
| Tocopherol (plant derived) | 1% | 1% |

TABLE 2

Canine Sebum Composition

| COMPONENTS | About % | Preferred % |
|---|---|---|
| Plant Sterol Esters | 42% | 42% |
| Jojoba Oil | 25% | 25% |
| Olive Oil | 20% | 20% |
| Safflower Oil | 7% | 7% |
| Almond Oil | 5% | 5% |
| Tocopherol (plant derived) | 1% | 1% |

TABLE 3

Canine Sebum Composition

| COMPONENTS | About % | Preferred % |
|---|---|---|
| Sterol Esters | 42% | 42% |
| Cholesterol | 9% | 9% |
| Wax Diesters | 32% | 32% |
| Triglycerides | 7% | 7% |

TABLE 4

Jojoba Oil Composition

| COMPONENTS | About % | Preferred % |
|---|---|---|
| Palmitic Acid | 3% | 3% |
| Palmitoleic Acid | 1% | 1% |
| Stearic Acid | 1% | 1% |
| Oleic Acid | 5-15% | 5-15% |
| Linoleic Acid | 5% | 5% |
| Linolenic Acid | 1% | 1% |
| Arachidic Acid | 0.5% | 0.5% |
| Eicosenoic Acid | 65-80% | 65-80% |
| Behenic Acid | 0.5% | 0.5% |
| Erucic Acid | 10-20% | 10-20% |
| Lignoceric Acid | 5% | 5% |

TABLE 5

Olive Oil Composition

| COMPONENTS | About % | Preferred % |
|---|---|---|
| Palmitic Acid | 13% | 13% |
| Stearic Acid | 3% | 3% |
| Oleic Acid | 71% | 71% |
| Linoleic Acid | 10% | 10% |
| Alpha Linolenic Acid | 1% | 1% |

TABLE 6

Peanut Oil Composition

| COMPONENTS | About % | Preferred % |
|---|---|---|
| Palmitic Acid | 11% | 11% |
| Stearic Acid | 2% | 2% |
| Oleic Acid | 48% | 48% |
| Linoleic Acid | 32% | 32% |
| Unidentified | 7% | 7% |

TABLE 7

Safflower Oil Composition

| COMPONENTS | About % | Preferred % |
|---|---|---|
| Myristic | 0.5% | 0.5% |
| Oleic | 13-21% | 13-21% |
| Palmitic Acid | 3-6% | 3-6% |
| Linoleic | 73-79% | 73-79% |
| Linolenic | 0.2% | 0.2% |
| Stearic | 1-4% | 1-4% |

In broad embodiment, the present invention is a plant derived substitute for canine sebum that offers the protection, performance and functional equivalence of naturally produced canine sebum on the hair and skin of dogs.

The advantages of the present invention include, without limitation, ease of formulation, low cost, plasticization of hair and skin keratin, increased conditioning and improvement of hair feel, anti-microbial activity, thermo-regulatory contribution, shine improvement, aid in the reduction and control of topical parasites.

While the foregoing written description of the invention enables one of ordinary skill to make and use what is considered presently to be the best mode thereof, those of ordinary skill will understand and appreciate the existence of the unique composition of canine sebum and the value of having a plant derived canine sebum substitute which is the embodiment, method and example herein provided. The invention should therefore not be limited by the above described embodiment, method and examples, but by all embodiments and methods within the scope and spirit of the invention.

In operation, the canine sebum substitute may be used on the hair and skin of dogs or be added to pet grooming products as needed to provide the benefits provided by canine sebum. These pet grooming products include shampoos, conditioners, shine sprays, and hair detanglers. The composition may be prepared by simple mixing at room temperature. All oils are soluble together.

It will thus be seen that the objects set forth above, among those made apparent from the preceding description are efficiently attained and since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

What is claimed is:

1. A composition of unadulterated plant derived oils to augment canine sebum comprising a plurality of soluble oils including about 42% of plant sterol esters, about 25% jojoba oil, about 20% olive oil, about 7% safflower oil, about 5% almond oil, and about 1% tocopherol or tocopherol acetate all by weight of the composition.

2. The composition of claim 1 wherein said jojoba oil comprises about 3% palmitic acid, about 1% palmitoleic acid, about 1% stearic acid, between about 5% to 15% oleic acid, about 5% linoleic acid, about 1% linolenic acid, about 0.5% arachidic acid, between about 65% to 80% eicosenoic acid, about 0.5% behenic acid, between about 10% to 20% erucic acid, and about 5% lignoceric acid all by weight of said jojoba oil.

3. The composition of claim 1 wherein said olive oil comprises about 13% palmitic acid, about 3% stearic acid, about 71% oleic acid, about 10% linoleic acid, and about 1% alpha linolenic acid all by weight of said olive oil.

4. The composition of claim 1 wherein said safflower oil comprises about 0.5% myristic acid, about 13% to 21% oleic acid, about 3% to 6% palmitic acid, about 73% to 79% linoleic acid, about 0.2% linolenic, and about 1% to 4% stearic acid all by weight of said safflower oil.

5. The composition of claim 1 wherein said jojoba oil comprises about 3% palmitic acid, about 1% palmitoleic acid, about 1% stearic acid, between about 5% to 15% oleic acid, about 5% linoleic acid, about 1% linolenic acid, about 0.5% arachidic acid, between about 65% to 80% eicosenoic acid, about 0.5% behenic acid, between about 10% to 20% erucic acid, and about 5% lignoceric acid all by weight of said jojoba oil; said olive oil comprises about 13% palmitic acid, about 3% stearic acid, about 71% oleic acid, about 10% linoleic acid, and about 1% alpha linolenic acid all by weight of said olive oil; and said safflower oil comprises about 0.5% myristic acid, about 13% to 21% oleic acid, about 3% to 6% palmitic acid, about 73% to 79% linoleic acid, about 0.2% linolenic, and about 1% to 4% stearic acid all by weight of said safflower oil.

6. A composition of unadulterated plant derived oils to augment canine sebum comprising a plurality of soluble oils including about 42% of plant sterol esters, about 25% jojoba oil, about 20% olive oil, about 7% peanut oil, about 5% almond oil, and about 1% tocopherol or tocopherol acetate all by weight of the composition.

7. The composition of claim 6 wherein said jojoba oil comprises about 3% palmitic acid, about 1% palmitoleic acid, about 1% stearic acid, between about 5% to 15% oleic acid, about 5% linoleic acid, about 1% linolenic acid, about 0.5% arachidic acid, between about 65% to 80% eicosenoic acid, about 0.5% behenic acid, between about 10% to 20% erucic acid, and about 5% lignoceric acid all by weight of said jojoba oil.

8. The composition of claim 6 wherein said olive oil comprises about 13% palmitic acid, about 3% stearic acid, about 71% oleic acid, about 10% linoleic acid, and about 1% alpha linolenic acid all by weight of said olive oil.

9. The composition of claim 6 wherein said peanut oil comprises about 48% oleic acid, about 11% palmitic acid, about 32% linoleic acid, and about 2% stearic acid all by weight of said peanut oil.

10. The composition of claim 6 wherein said jojoba oil comprises about 3% palmitic acid, about 1% palmitoleic acid, about 1% stearic acid, between about 5% to 15% oleic acid, about 5% linoleic acid, about 1% linolenic acid, about 0.5% arachidic acid, between about 65% to 80% eicosenoic acid, about 0.5% behenic acid, between about 10% to 20% erucic acid, and about 5% lignoceric acid all by weight of said jojoba oil; said olive oil comprises about 13% palmitic acid, about 3% stearic acid, about 71% oleic acid, about 10% linoleic acid, and about 1% alpha linolenic acid all by weight of said olive oil; and said peanut oil comprises about 48% oleic acid, about 11% palmitic acid, about 32% linoleic acid, and about 2% stearic acid all by weight of said peanut oil.

\* \* \* \* \*